(12) United States Patent
Nakatogawa et al.

(10) Patent No.: US 7,521,563 B2
(45) Date of Patent: Apr. 21, 2009

(54) HYDROXAMIC ACID DERIVATIVE AND MEDICINE CONTAINING THE SAME AS ACTIVE INGREDIENT

(75) Inventors: Kiyoshi Nakatogawa, Shizuoka (JP); Masamichi Takagi, Shizuoka (JP); Makoto Akashima, Shizuoka (JP)

(73) Assignee: Shizuoka Coffein Co., Ltd., Shizuoka (JP)

( * ) Notice: Subject to any disclaimer, the term of this patent is extended or adjusted under 35 U.S.C. 154(b) by 99 days.

(21) Appl. No.: 11/659,810

(22) PCT Filed: Aug. 10, 2004

(86) PCT No.: PCT/JP2004/011473
§ 371 (c)(1),
(2), (4) Date: Feb. 9, 2007

(87) PCT Pub. No.: WO2006/016399
PCT Pub. Date: Feb. 16, 2006

(65) Prior Publication Data
US 2007/0208065 A1    Sep. 6, 2007

(51) Int. Cl.
C07D 263/30 (2006.01)
C07D 413/00 (2006.01)
C07D 277/20 (2006.01)
A61K 31/42 (2006.01)
A61K 31/425 (2006.01)

(52) U.S. Cl. .................. 548/235; 548/100; 548/146; 548/215; 548/202; 514/359; 514/365; 514/374

(58) Field of Classification Search .................. 548/100, 548/146, 202, 215, 235; 514/359, 365, 374
See application file for complete search history.

(56) References Cited

U.S. PATENT DOCUMENTS

| 3,538,107 | A | 11/1970 | Hepworth et al. |
| 3,578,671 | A | 5/1971 | Brown |
| 5,137,897 | A | 8/1992 | Thorwart et al. |
| 6,696,477 | B2 * | 2/2004 | Talley et al. ............... 514/406 |
| 2001/0056189 | A1 | 12/2001 | Talley et al. |
| 2003/0073722 | A1 | 4/2003 | Talley et al. |

FOREIGN PATENT DOCUMENTS

| JP | 5-17459 A | 1/1993 |
| JP | 9-503222 | 4/1995 |
| JP | 9-209940 | 9/1995 |
| JP | 2000-503312 | 7/1997 |
| JP | 2002-80445 | 3/2002 |
| JP | 2004-250401 A | 9/2004 |
| WO | WO 96/38418 | 12/1996 |
| WO | WO 99/61412 | 12/1999 |
| WO | WO 02/074298 | 9/2002 |
| WO | WO 2005/040161 A | 5/2005 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Hirano et al, "*Excessive production of interleukin 6/B cell stimulatory factor-2 in rheumatoid arthritis*", Eur. J. Immunol. 1988, 18: 1797-1801.
Yoshizaki et al, "*Pathogenic Significance of Interleukin-6 (IL-6/BSF-2) in Castleman's Disease*", Blood, vol. 74, No. 4 (Sep. 1989): pp. 1360-1367.
Allergy/Immunology, vol. 10, No. 9, 2003, pp. 67-75.
Yujia Dai, et al, "A Novel Series of Histone Deacetylase Inhibitors Incorporating Hetero Aromatic Ring Systems as Connection Units", Bioorganic & Medicinal Chemistry Letters, vol. 13, No. 21, 2003, pp. 3817 to 3820.

* cited by examiner

Primary Examiner—Kamal A Saeed
Assistant Examiner—Samantha L Shterengarts
(74) Attorney, Agent, or Firm—Sughrue Mion, PLLC

(57) ABSTRACT

A compound which inhibits the production of IL-6 and/or TNFα by inflammatory cytokines and is useful in the prevention of or treatments for diseases such as various inflammatory diseases in which these cytokines participate and autoimmune diseases. It is a hydroxamic acid derivative represented by the following formula (1): (1) (wherein A and B each represents phenyl, etc.; n is an integer of 1 to 8; and Y represents oxygen or sulfur). This compound has excellent interleukin-6 and/or TNFα production inhibitory activity and is useful as a therapeutic agent for various inflammatory diseases, autoimmune diseases, etc.

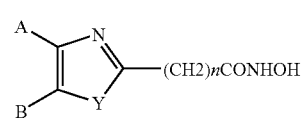

(1)

13 Claims, No Drawings

HYDROXAMIC ACID DERIVATIVE AND MEDICINE CONTAINING THE SAME AS ACTIVE INGREDIENT

TECHNICAL FIELD

The present invention relates to a hydroxamic acid derivative and a medicine containing the same as an active ingredient. More particularly, the present invention relates to a hydroxamic acid derivative having a basic chemical structure of N-hydroxy-2-thiazole or oxazole alkyl amide and a medicine containing the same as an active ingredient and being effective as an inhibitor of production of interleukin-6 (IL-6) and/or TNFα.

BACKGROUND ART

Various kinds of cytokines have functions such as an action of control of immune responses, an antitumor action, an antivirus action and regulation of cell proliferation/differentiation and play important roles in bio-defense reactions such as inflammatory reactions, hematopoiesis, bone metabolisms, allergic reactions and autoimmune diseases. Inflammatory cytokines such as IL-6 and TNFα are produced from various kinds of cells including immunological cells such as macrophages, and fibroblasts, vascular endothelial cells, osteoblasts and the like, and exhibit a variety of physiological activities such as induction of differentiation of B cells to antibody chain producing cells, induction of production of an acute phase protein from liver cells, and directly acting on a bone marrow-derived macrophage as precursor cells of osteoclasts to induce differentiation of the macrophage to osteoclasts. It has been found that in autoimmune diseases such as rheumatoid arthritis and Castleman disease, a large amount of IL-6 and TNFα is produced from an arthrosynovialis and a large amount of IL-6 is produced from a hypertrophic lymph node of a Castleman disease patient, and IL-6 and TNFα are considered to be a cause of these diseases (Non-Patent Document 1; Non-Patent Document 2; Non-Patent Document 3).

Hydroxamic acid derivatives, of which the usefulness as inhibitors of cytokines has been disclosed, include the following.

(1) Patent Document 1 discloses that a hydroxamic acid derivative represented by general formula (a) is an inhibitor of release of TNFα from cells and inhibits metallo-proteinase involved in disorganization.

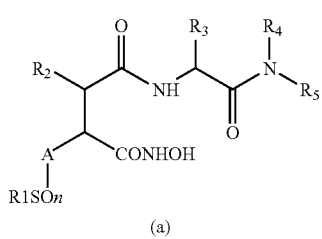

(a)

(2) Patent Document 2 discloses that an imidazole substituted hydroxamic acid derivative represented by general formula (b) is useful as an inhibitor of a matrix degradable metalloproteinase.

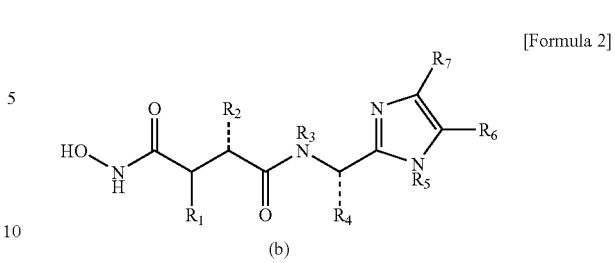

(b)

(3) Patent Document 3 discloses that a hydroxamic acid derivative represented by general formula (c) has an action of suppressing production of TNFα.

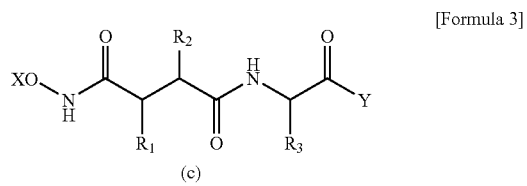

(c)

(4) Patent Document 4 discloses that a hydroxamic acid derivative represented by general formula (d) inhibits formation of human CD23 and is useful for treatment of symptoms related to overproduction of soluble CD23, such as autoimmune diseases and allergies.

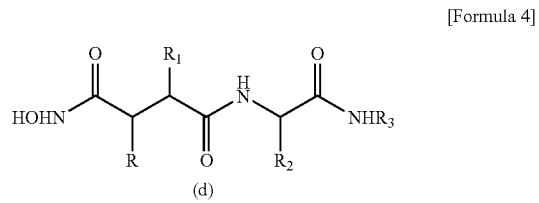

(d)

(5) Patent Document 5 discloses that a hydroxamic acid derivative having a hydroxyl group at 6-position, which is represented by general formula (e), suppresses production of IL-6. Requirements for stereoisomers of the hydroxyl group at 6-position are disclosed in the specification of the patent document, and in the invention thereof, the hydroxyl group at 6-position is a necessary structural element in expression of an IL-6 production suppressing activity.

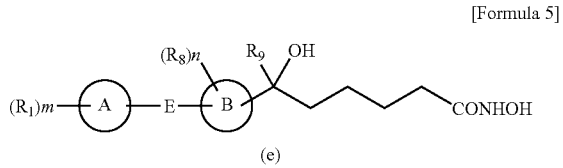

(e)

(6) Patent Document 6 discloses that a hydroxamic acid derivative represented by formula (f) suppresses production of IL-6. However, in this publication, compounds specifically described are limited to compounds of general formula (f) in which ring A and ring B are phenyl groups.

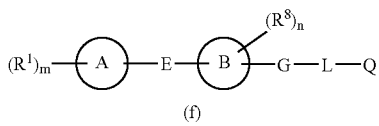

[Formula 6]

(f)

(7) Patent Document 7 discloses that an oxazole compound represented by formula (g) is effective as an anti-inflammatory agent. However, suppression of production of IL6 and/or TNFα is not described.

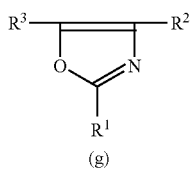

[Formula 7]

(g)

Patent Document 1: JP-A-9-503222
Patent Document 2: JP-A-9-509940
Patent Document 3: WO 99/61412 Pamphlet
Patent Document 4: JP-A-2000-503312
Patent Document 5: JP-A-2002-80445
Patent Document 6: WO 2002/074298 Pamphlet
Patent Document 7: U.S. Pat. No. 3,578,671
Non-Patent Document 1: Eur. J. Immunol, 18:1797-1801 (1988)
Non-Patent Document 2: Blood, 74(4):1360, (1989)
Non-Patent Document 3: Allergy/Immunology, Vol. 10, No. 9, 67-75 (2003)

DISCLOSURE OF THE INVENTION

Problems to be Solved by the Invention

The present invention provides compounds which suppress production of IL6 and/or TNFα and are useful for prevention or treatment of various kinds of inflammatory diseases, autoimmune diseases and the like in which such cytokines are involved.

Means For Solving the Problems

As a result of conducting vigorous studies on compounds having an activity of suppressing production of, particularly, IL6 and/or TNFα, the present inventors have found that hydroxamic acid derivatives having a basic chemical structure of N-hydroxy-2-thiazole or oxazole alkyl amide achieve the object. These compounds have not been previously synthesized and are novel compounds suppressing production of IL6 and/or TNFα, which have been newly found by the inventors.

Namely, the present invention relates to compounds represented by formula (1):

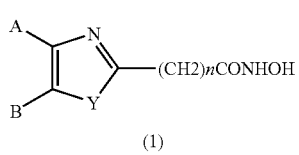

[Formula 8]

(1)

wherein A and B, which are same or different, each represent a hydrogen atom, an alkyl group, or an aryl group which may have a substituent, Y represents an oxygen atom or a sulfur atom, and n represents an integer of 1 to 8, except that A and B are phenyl groups, Y is an oxygen atom and n is an integer of 2, or pharmaceutically acceptable salts or solvates thereof, or prodrugs thereof.

Further, the present invention relates to medicines having as an active ingredient the compounds of formula (1), or pharmaceutically acceptable salts or solvates thereof, or prodrugs thereof.

Further, the present invention relates to inhibitors of production of interleukin-6 and/or TNFα having as an active ingredient the compounds of formula (1) (including the case that A and B are phenyls, Y is an oxygen atom and n is an integer of 2), or pharmaceutically acceptable salts or solvates thereof, or prodrugs thereof.

Advantages of the Invention

The compounds of the present invention, or pharmaceutically acceptable salts or solvates thereof, or prodrugs thereof strongly suppress production of IL-6 and/or TNFα of inflammatory cytokines, while they have no or very low toxicity to cells. Therefore, the compounds of the present invention are useful as prophylactics or therapeutics for various kinds of inflammatory diseases, septicemia, multiple myeloma, osteoporosis, rheumatoid arthritis, Castleman disease, inflammatory colitis, autoimmune disease and the like.

BEST MODE FOR CARRYING OUT THE INVENTION

In the compounds represented by formula (1) of the present invention, A and B, which are same or different, each represent a hydrogen atom, an alkyl group, or an aryl group which may have a substituent, Y represents an oxygen atom or a sulfur atom, and n represents an integer of 1 to 8.

Here, alkyls groups include, for example, linear or branched alkyl groups having 1 to 8 carbon atoms, such as a methyl group, an ethyl group, a propyl group, an isopropyl group, a butyl group, an isobutyl group, a sec-butyl group, a tert-butyl group, a pentyl group, a heptyl group and an octyl group.

Aryl groups include, for example, aryl groups having 6 to 10 carbon atoms, such as a phenyl group and a naphthyl group. The aryl group is preferably a phenyl group. These aryl groups may have substituents, and the substituents include, for example, halogen atoms such as a chlorine atom, a bromine atom and a fluorine atom; linear or branched lower alkyls having 1 to 6 carbon atoms, such as a methyl group, an ethyl group, a propyl group, an isopropyl group, a butyl group, an isobutyl group, a sec-butyl group and a tert-butyl group; linear or branched halogenated lower alkyls having 1 to 6 carbon atoms, such a trifluoromethyl group, a trichloromethyl group and a 2,2,2-trifluoroethyl group; linear or branched lower alkenyl groups having 2 to 6 carbon atoms, such as a vinyl group, an aryl group, a propens-1-yl group, a butene-1-yl group and a pentene-1-yl group; linear or branched lower alkynyl groups having 2 to 6 carbon atoms, such as an ethynyl group, a propine-1-yl group, a butyne-1-yl group and a 1-methylbutyne-3-yl group; linear or branched lower alkoxy groups having 1 to 6 carbon atoms, such as a methoxy group, an ethoxy group, a propoxy group, an isopropoxy group, a butoxy group, an isobutoxy group, a sec-butoxy group and a tert-butoxy group; acyl groups having 1 to 6 carbon atoms, such as a formyl group, an acetyl group and a propanoyl group; acyloxy groups having 2 to 6 carbon atoms, such as an acetyloxy group and a propanoyloxy group; lower alkyl substituted amino groups having 1 to 6 carbon atoms, such as a methylamino group, a dimethylamino group, an ethylamino group and a diethylamino group; alkyloxycarbonyl groups having 2 to 6 carbon atoms, such as a methyloxycarbonyl group, an ethyloxycarbonyl group and a butyloxycarbonyl group; lower alkylmercapto groups having 1 to 6 carbon atoms, such as a methylmercapto group, an ethylmercapto group and a butylmercapto group; a hydroxyl group; a carboxyl group; a mercapto group; a nitro group; and a cyano group.

In formula (1), preferably, A and B, which are same or different, each are a hydrogen atom, an alkyl group, a phenyl group, or a phenyl group substituted with a halogen atom, a lower alkyl group, a lower alkoxy group or a halogenated lower alkyl group.

In formula (1), n represents an integer of 1 to 8, n is preferably an integer of 5 or 6, and n is especially preferably an integer of 5.

The compounds represented by formula (1) of the present invention may be replaced by pharmaceutically acceptable salts or solvates thereof, or prodrugs thereof as required. Pharmaceutically acceptable salts include metal salts, organic amine salts and acid addition salts. Specifically, the metal salts include, for example, alkali metals such as sodium salts and potassium salts; and alkalin-earth metal salts such as magnesium salts and calcium salts. The acid addition salts include, for example, inorganic acid salts such as hydrochlorides, phosphates and sulfates and organic acid salts such as methane sulfonic acid salts. The solvates include hydrates with water and solvates with solvents such as methanol and ethanol. The prodrugs of the compounds of formula (1) include compounds that are converted into the compounds of formula (1) by gastric acid and enzymes in vivo. Specifically, the prodrugs include, for example, compounds in which the hydroxyl group of hydroxamic acid in the compound of formula (1) is acylated with an acyl group having 2 to 6 carbon atoms, such as an acetyl group or a propyl group; and compounds in which the hydroxyl group of hydroxamic acid is alkylated with an alkyl group having 1 to 6 carbon atoms, such as a methyl group, an ethyl group or a propyl group. One form of the prodrug may be a compound in which a ring is formed with involvement of the hydroxyl group and amide of hydroxamic acid. These salts, solvates and prodrugs can be easily produced from the compounds of formula (1) by a publicly known method.

In the present invention, compounds selected from the group of compounds described below are preferable specific examples.

5-[4-(1,1-dimethylethyl)phenyl]-N-hydroxy-4-phenyl-2-oxazolehexanamide,
5-(4-chlorophenyl)-N-hydroxy-4-phenyl-2-oxazolehexanamide,
5-(4-fluorophenyl)-N-hydroxy-4-phenyl-2-oxazolehexanamide,
N-hydroxy-4,5-bis(4-methylphenyl)-2-oxazolehexanamide,
N-hydroxy-4,5-bis(4-methoxyphenyl)-2-oxazolehexanamide,
4,5-bis(4-fluorophenyl)-N-hydroxy-2-oxazolehexanamide,
N-hydroxy-4,5-bis[4-(trifluoromethyl)phenyl]-2-oxazolehexanamide,
5-(4-fluorophenyl)-N-hydroxy-4-phenyl-2-thiazolehexanamide,
5-(4-chlorophenyl)-N-hydroxy-4-phenyl-2-thiazolehexanamide,
N-hydroxy-5-(4-methylphenyl)-4-phenyl-2-thiazolehexanamide,
4-(4-fluorophenyl)-N-hydroxy-5-phenyl-2-thiazolehexanamide,
4-(4-chlorophenyl)-N-hydroxy-5-phenyl-2-thiazolehexanamide,
N-hydroxy-4-(4-methylphenyl)-5-phenyl-2-thiazolehexanamide,
N-hydroxy-4,5-diphenyl-2-thiazolehexanamide,
N-hydroxy-5-phenyl-2-oxazolehexanamide,
5-(4-bromophenyl)-N-hydroxy-2-oxazolehexanamide,
N-hydroxy-4-(4-methoxyphenyl)-2-oxazolehexanamide,
4-(4-chlorophenyl)-N-hydroxy-2-oxazolehexanamide,
4-(4-fluorophenyl)-N-hydroxy-2-oxazolehexanamide,
5-(4-bromophenyl)-N-hydroxy-2-thiazolehexanamide,
N-hydroxy-4,5-dipropyl-2-oxazolehexanamide,
N-hydroxy-5-methyl-4-phenyl-2-oxazolehexanamide,
N-hydroxy-4-methyl-5-phenyl-2-oxazolehexanamide,
N-hydroxy-4,5-diphenyl-2-oxazoleheptanamide, and
N-hydroxy-4,5-diphenyl-2-oxazolehexanamide.

Method for production of compounds of the invention

Any of the compounds represented by formula (1) of the present invention can be produced by a publicly known method. Representative methods for production of these compounds will be described below.

For example, the compounds represented by formula (1) of the present invention can be synthesized by synthesizing a 1,3-azole derivative substituted with an alkylcarboxylic acid in 2-position of the basic backbone of 1,3-oxazole or thiazole, and then converting the carboxylic group of the 1,3-azole derivative into a hydrooxime group.

The 1,3-azole derivative substituted with an alkylcarboxylic acid in 2-position of the basic backbone of 1,3-oxazole or thiazole is obtained in accordance with scheme A described below.

Scheme A

[Formula 9]

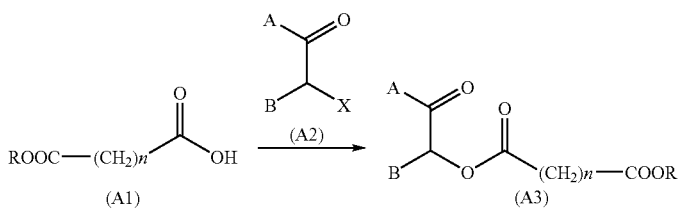

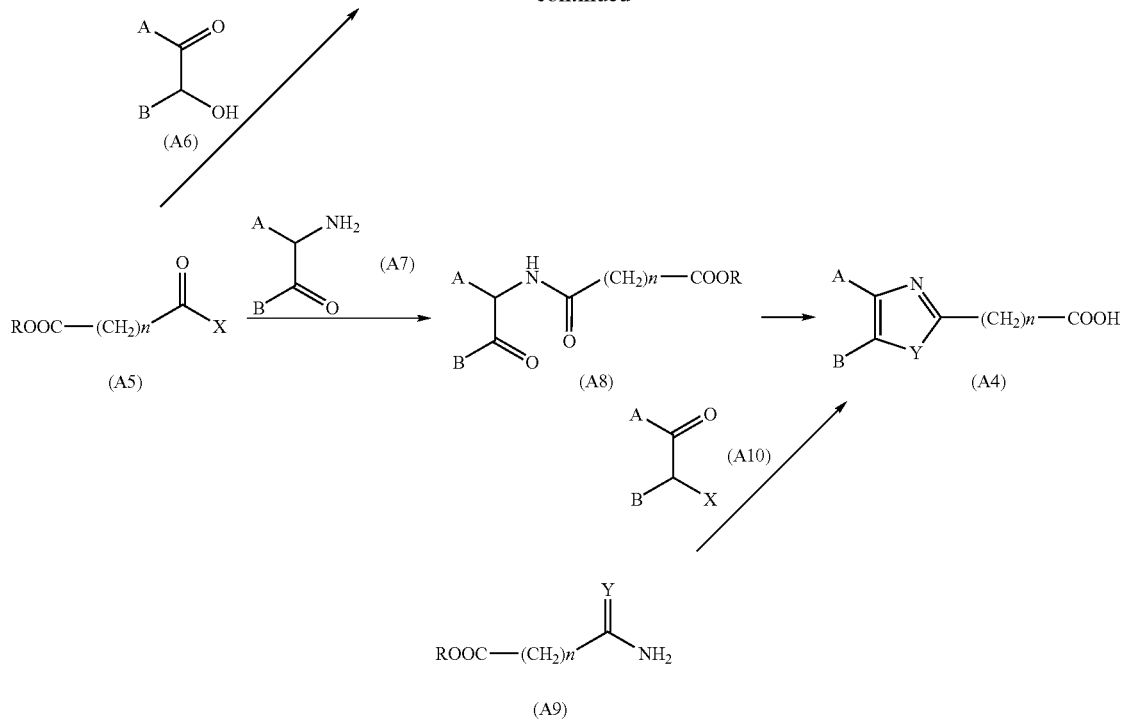

In formula 9, A and B represent A and B in formula (1), and Y is an oxygen atom or a sulfur atom. n represents an integer of 1 to 8, R represents an alkyl group, and X represents a halogen atom.

An oxazole derivative of formula (A4) in which Y is an oxygen atom is obtained by reacting a carboxylic acid represented by formula (A1) and an α-haloketone form represented by formula (A2) under presence of a base such as potassium carbonate and heating the obtained ester form represented by formula (A3) with a nitrogen source, for example urea or ammonium acetate, in acetic acid (reference: Heterocyclic Compounds, Wiley & Sons, Inc., 5, 302-323).

The ester form represented by formula (A3) is also obtained by reacting an acid halide form represented by formula (A5) with an α-hydroxyketone form represented by formula (A6) at room temperature to 100° C. under presence of pyridine, trialkylamine or the like.

The oxazole derivative of formula (A4) in which Y is an oxygen atom is also obtained by reacting the acid halide form represented by formula (A5) with an α-aminoketone form represented by formula (A7) at room temperature to 100° C. under presence of pyridine, trialkylamine or the like and heating the obtained amide form represented by formula (A8) under presence of a dehydrating agent such as phosphorous pentachloride.

Alternatively, the oxazole derivative can also be obtained by heating an acid amide compound of formula (A9) in which Y is an oxygen atom and an α-haloketone form represented by formula (A10) (reference: Dai Yukikagaku, 15,6-45).

A thiazole derivative of formula (A4) in which Y is a sulfur atom is obtained by heating the amide form represented by formula (A8) together with diphosphoric pentasulfide.

The thiazole derivative can also be obtained by reacting a thioamide compound of formula (A9) in which Y is a sulfur atom and the α-haloketone form represented by formula (A10) at room temperature to 50° C.

In scheme A, the carboxylate in formula (A3) and formula (A8) can be derived to a carboxylic acid by forming a 1,3-azole ring, and then treating the ester together with, for example, aqueous sodium hydroxide at room temperature or under reflux for several hours in accordance with a conventional method, followed by acidic precipitation.

The above method is illustrative, and other similar known methods may also be used.

For obtaining the hydroxamic acid derivative of the present invention by converting into a hydrooxime group the 1,3-azole derivative synthesized in the manner described above, synthesis is carried out in accordance with scheme B described below.

Scheme B

[Formula 10]

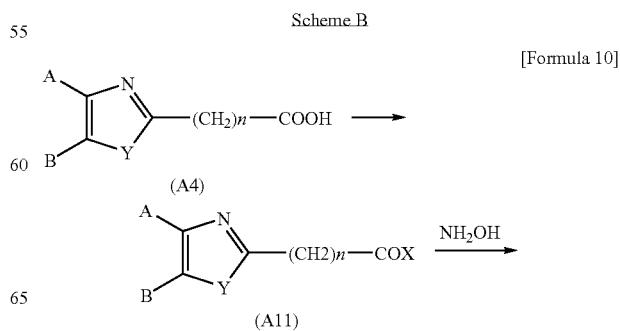

-continued

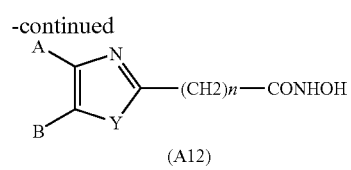

(A12)

In formula 10, A and B represent A and B in formula (1), and Y represents an oxygen atom or a sulfur atom. X represents a halogen atom, and n represents an integer of 1 to 8.

For conversion of the carboxylic acid derivative obtained in accordance with scheme A into a hydroxamic acid derivative, a carboxylic acid derivative represented by formula (A4) can be converted into an acid halide form represented by formula (A11) with a halogenated thionyl or the like in accordance with a conventional method, and then reacted with hydroxylamine under a base such as a trialkylamine to obtain a hydroxamic acid derivative represented by formula (A12).

The above method is illustrative, and other similar known methods may also be used.

Medicines having as an active ingredient hydroxamic acid derivatives of formula (1) manufactured in the manner described above, pharmaceutically acceptable salts or solvates thereof, or prodrugs thereof may be administered normally to mammals (including human patients) as oral dosage drugs including tablets, capsules, powders, subtle granules, liquid formulations and syrups, rectal dosage drugs or injections. The compound of the present invention may be administered as one therapeutic or as a mixture with other therapeutics.

They may be administered alone, but are generally administered in the form of a pharmaceutical composition. Those preparations may be produced by a conventional method with pharmacologically and pharmaceutically acceptable additives added thereto. Namely, for oral dosage drugs such as tablets, capsules, powders, subtle granules and syrups, normal additives such as excipients, lubricants, binders, disintegrators, wetting agents and coatings may be used. The liquid formulation for oral dosage may be in the form of an aqueous or oil suspension, solution, emulsion, syrup, elixir or the like, or may be provided as a dry syrup which is prepared with water or another suitable solvent before use. The above liquid formulation may contain normal additives such as suspending agents, flavors, diluting agents or emulsifiers. The medicine may be administered as a suppository when it is intrarectally administered. The suppository has as a base an appropriate substance such as cacao oil, lauric oil, macrogol, glycerogelatin, Witepsol, sodium stearate or a mixture thereof, and emulsifiers, suspending agents, preservatives and the like may be added thereto as required. For the injection, preparation components such as distilled water for injection capable of forming an aqueous or before-use soluble formulation, a physiological saline, a 5% glucose solution, a solubilizer or solubilizing agent such as propylene glycol, a pH regulator, a tonicity adjusting agent and a stabilizer are used. Specific examples of excipients and the like used in the above composition will be described below.

Excipients include magnesium aluminate metasilicate, magnesium silicate, magnesium carbonate, calcium hydrogen phosphate, abicel, various kinds of starches, dextrin, carboxymethyl starch (CMS) and lactose. Binders include ethylcellulose (EC), hydroxypropylmethylcellulose (HPMC), hydroxypropylcellulose (HPC), sodium alginate, gelatin, polyvinyl pyrolidone (PVP). Disintegrating agents include synthetic aluminum silicate, magnesium aluminate metasilicate, abicel and hydroxypropyl starch (CPS). Anti-caking agents include light anhydrous silicic acid and synthetic aluminum silicate. Lubricants include synthetic aluminum silicate, anhydrous silicic acid, talc and abicel. Sweeteners include mannitol, citric acid, sodium citrate and sugar.

Emulsifiers include gelatin, macrogol (PEG), propylene glycol fatty acid esters, polyoxyethylene polyoxypropylene glycol and phospholipids. Stabilizers include propylene glycol fatty acid esters, polyoxyethylene polyoxypropylene glycol and various kinds of natural and synthetic cyclodextrins. Absorption promoting agents include propylene glycol fatty acid esters, polyoxyethylene polyoxypropylene glycol, sodium lauryl sulfate and various kinds of natural and synthetic cyclodextrins. Solubilizing agents include ethanol, polyethylene glycol, propylene glycol fatty acid esters, propylene glycol, and various natural/synthetic cyclodextrins. Suspending agents include sodium alginate, gelatin, propylene glycol and sodium lauryl sulfate. Coatings include magnesium silicate, talc, titanium oxide, calcium carbonate and triacetylene, carboxymethylethylcellulose (CMEC). Coloring agents include tar dyes and caramels.

When the compound of the present invention is administered to a human, a dose depends on the age, the symptom and the like of the patient, but in the case of an adult, it is normally about 1 mg to 1000 mg/person/day for the intrarectal dosage drug, and about 1 to 500 mg/person/day for the injection. However, these values are only illustrative, and the dose is appropriately increased or decreased according to various kinds of conditions such as the symptom of the patient.

The present invention will now be described specifically using examples of production, preparations and test of the compounds of the present invention, but the present invention is not limited to these examples.

EXAMPLE 1

Production of 5-[4-(1,1-dimethylethyl)phenyl]-N-hydroxy-4-phenyl-2-oxazolehexanamide (Compound 1)

(1) 5-[4-(1,1-dimethylethyl)phenyl]-4-phenyl-2-oxazole hexanoic acid ethyl ester Pyridine (3.0 mL) and ethyl 6-(chloroformyl) hexanoate (4.1 g) were added to 4'-tert.-butylbenzoin (3.0 g) in 1,4-dioxane (50 mL), and the resultant mixture was reacted at room temperature for 2.5 hours. The reaction liquid was added to water (200 mL), and the resultant mixture was stirred, and an object material was then extracted with ethyl acetate (100 mL). The organic layer washed with water, and then condensed under a reduced pressure to obtain an ester form (6.4 g).

Ammonium acetate (4.4 g) was added to the ester form (6.4 g) in acetic acid (30 mL), and the resultant mixture was reacted under reflux for 1 hour. Water (100 mL) was added to the reaction liquid, and an object material was extracted with ethyl acetate (100 mL). The organic layer washed with water, dehydrated with magnesium sulfate, and condensed under a reduced pressure to obtain a crude product. The crude product was purified with a silica gel column (chloroform) to obtain a subject compound (4.48 g, Y=96%)

(2) 5-[4(1,1-dimethylethyl)phenyl]-4-phenyl-2-oxazolehexanoic acid

A 18% aqueous potassium hydroxide solution (10 mL) was added to the compound (4.24 g) obtained in the above section (1) in ethanol (40 ml), and the resultant mixture was reacted at room temperature for 2.5 hours. The reaction liquid was condensed under a reduced pressure, the residue was dissolved in water (50 mL) by heating, the resultant solution was subjected to acidic precipitation by adding diluted hydrochloric acid, and an object material was extracted with ethyl acetate (200 mL). The organic layer was washed with water, dehydrated with magnesium sulfate, and then condensed under a reduced pressure to obtain a crude product. The crude product was purified with a silica gel column (chloroform/methanol) to obtain a subject compound (3.00 g, Y=69%).

$^1$H-NMR(DMSO-d6/TMS): δ=1.29(9H,s) 1.53-2.34(8H, m) 2.82(2H,t,J=7 Hz) 7.32-7.63(9H,m)

(3) 5-[4-(1,1-dimethylethyl)phenyl]-N-hydroxy-4-phenyl-2-oxazolehexanamide (Compound 1)

The compound (1.50 g) obtained in the above section (2) was reacted with thionyl chloride (0.7 mL) in toluene (30 mL) under reflux for 30 minutes, and the reaction liquid was condensed under a reduced pressure to obtain an acid chloride.

The obtained acid chloride was dropped into a solution consisting of a hydroxylamine chloride (1.35 g), triethylamine (3.90 g) and 1,3-dimethyl-2-imidazolidinone (50 mL), and the resultant mixture was reacted over night. The reaction liquid was added to water (500 mL), diluted hydrochloric acid was added to pH≦3, and an object material was then extracted with ethyl acetate (200 mL). The organic layer washed with water, dehydrated with magnesium sulfate, and then condensed under a reduced pressure to obtain a crude product. The crude product was purified with a silica gel column (chloroform/methanol) to obtain a desired subject compound (1.02 g, Y=66%).

$^1$H-NMR(DMSO-d6/TMS): δ=1.29(9H,s) 1.50-1.98(8H, m) 2.82(2H,t,J=7 Hz) 7.32-7.71(9H,m) 8.46-8.95(1H,br) 9.99-10.66 (1H,br)

EXAMPLE 2

Production of 5-(4-chlorophenyl)-N-hydroxy-4-phenyl-2-oxazolehexanamide (Compound 2)

(1) 5-(4-chlorophenyl)-4-phenyl-2-oxazolehexanoic acid ethyl ester

The subject compound was produced in the same manner as in the section (1) of example 1.

(2) 5-(4-chlorophenyl)-4-phenyl-2-oxazolehexanoic acid

The subject compound was produced in the same manner as in the section (2) of example 1.

Melting point: 111° C.

$^1$H-NMR(DMSO-d6/TMS): δ=1.53-2.24(8H,m) 2.84(2H, t,J=7 Hz) 7.33-7.69(9H,m) 11.19-12.79(1H,br)

(3) 5-(4-chlorophenyl)-N-hydroxy-4-phenyl-2-oxazolehexanamide (Compound 2)

The desired subject compound was produced in the same manner as in the section (3) of example 1.

Melting point: 158° C.

$^1$H-NMR(DMSO-d6/TMS): δ=1.51-1.99(8H,m) 2.83(2H, t,J=7 Hz) 7.29-7.65(9H,m) 8.66(1H,s) 10.34(1H,s)

EXAMPLE 3

Production of 5-(4-fluorophenyl)-N-hydroxy-4-phenyl-2-oxazolehexanamide (Compound 3)

(1) 5-(4-fluorophenyl)-4-phenyl-2-oxazolehexanoic acid ethyl ester

The subject compound was produced in the same manner as in the section (1) of example 1.

(2) 5-(4-fluorophenyl)-4-phenyl-2-oxazolehexanoic acid

The subject compound was produced in the same manner as in the section (2) of example 1.

Melting point: 92° C.

$^1$H-NMR(DMSO-d6/TMS): δ=1.53-2.24(8H,m) 2.83(2H, t,J=7 Hz) 7.13-7.72(9H,m) 10.96-12.84(1H,br)

(3) 5-(4-fluorophenyl)-N-hydroxy-4-phenyl-2-oxazolehexanamide (Compound 3)

The desired subject compound was produced in the same manner as in the section (3) of example 1.

Melting point: 131° C.

$^1$H-NMR(DMSO-d6/TMS): δ=1.50-1.98(8H,m) 2.82(2H, t,J=7 Hz) 7.13-7.71(9H,m) 8.23-9.31(1H,br) 9.33-10.70(1H, br)

EXAMPLE 4

Production of N-hydroxy-4,5-bis(4-methylphenyl)-2-oxazolehexanamide (Compound 4)

(1) 4,5-bis(4-methylphenyl)-2-oxazolehexanoic acid ethyl ester

The subject compound was produced in the same manner as in the section (1) of example 1.

$^1$H-NMR(CDCl$_3$/TMS): δ=1.24(3H,t,J=7 Hz) 1.40-2.00 (6H,m) 2.20-2.45(8H,m) 2.84(2H,t,J=7 Hz) 4.12(2H,q,J=7 Hz) 7.07-7.60(8H,m)

(2) 4,5-bis(4-methylphenyl)-2-oxazolehexanoic acid

The subject compound was produced in the same manner as in the section (2) of example 1.

Melting point: 119° C.

$^1$H-NMR(DMSO-d6/TMS): δ=1.30-1.90(4H,m) 2.13-2.33(8H,m) 2.80(2H,t,J=7 Hz) 7.10-7.55(8H,m) 11.8(1H,brs)

(3) N-hydroxy-4,5-bis(4-methylphenyl)-2-oxazolehexanamide (Compound 4)

The desired subject compound was produced in the same manner as in the section (3) of example 1.

Melting point: 127° C.

$^1$H-NMR(DMSO-d6/TMS): δ=1.30-2.00(4H,m) 2.25-2.45(8H,m) 2.80(2H,t,J=7 Hz) 7.10-7.55(8H,m) 8.64(1H,s) 10.33(1H,s)

EXAMPLE 5

Production of N-hydroxy-4,5-bis(4-methoxyphenyl)-2-oxazolehexanamide

(1) 4,5-bis(4-methoxyphenyl)-2-oxazolehexanoic acid ethyl ester

The subject compound was produced in the same manner as in the section (1) of example 1.

$^1$H-NMR(CDCl$_3$/TMS): δ=1.24(3H,t,J=7 Hz) 1.50-2.00 (6H,m) 2.33(2H,t,J=6 Hz) 2.84(2H,t,J=7 Hz) 3.83(6H,s) 4.13 (2H,q,J=7 Hz) 7.76-7.00(4H,m) 7.27-7.65(4H,m)

(2) 4,5-bis(4-methoxyphenyl)-2-oxazolehexanoic acid

The subject compound was produced in the same manner as in the section (2) of example 1.

Melting point: 114° C.

$^1$H-NMR(DMSO-d6/TMS): δ=1.35-1.92(6H,m) 2.23(2H, t,J=7 Hz) 2.79(2H,t,J=7 Hz) 3.78-3.79(6H,m) 6.87-7.07(4H, m) 7.39-7.57(4H,m)

(3) N-hydroxy-4,5-bis(4-methoxyphenyl)-2-oxazolehexanamide (Compound 5)

The desired subject compound was produced in the same manner as in the section (3) of example 1.

Melting point: 119° C.

$^1$H-NMR(DMSO-d6/TMS): δ=1.23-2.00(6H,m) 2.79(2H, t,J=7 Hz) 3.78-3.79(6H,m) 6.87-7.07(4H,m) 7.39-7.57(4H, m) 8.63(1H,s) 10.33(1H,s)

EXAMPLE 6

Production of 4,5-bis(4-fluorophenyl)-N-hydroxy-2-oxazolehexanamide (Compound 6)

(1) 4,5-bis(4-fluorophenyl)-2-oxazolehexanoic acid ethyl ester

The subject compound was produced in the same manner as in the section (1) of example 1.

(2) 4,5-bis(4-fluorophenyl)-2-oxazolehexanoic acid

The subject compound was produced in the same manner as in the section (2) of example 1.

$^1$H-NMR(DMSO-d6/TMS): δ=1.52-2.23(8H,m) 2.83(2H, t,J=7 Hz) 7.08-7.73(8H,m)

(3) 4,5-bis(4-fluorophenyl)-N-hydroxy-2-oxazolehexanamide (Compound 6)

The desired subject compound was produced in the same manner as in the section (3) of example 1.

Melting point: 134° C.

$^1$H-NMR(DMSO-d6/TMS): δ=1.51-1.99(8H,m) 2.82(2H, t,J=7 Hz) 7.09-7.71(8H,m) 8.67(1H,brs) 10.33(1H,brs)

EXAMPLE 7

Production of N-hydroxy-4,5-bis[4-(trifluoromethyl) phenyl]-2-oxazolehexanamide (Compound 7)

(1) 4,5-bis[4-(trifluoromethyl)phenyl]-2-oxazolehexanoic acid ethyl ester

The subject compound was produced in the same manner as in the section (1) of example 1.

(2) 4,5-bis[4-(trifluoromethyl)phenyl]-2-oxazolehexanoic acid

The subject compound was produced in the same manner as in the section (2) of example 1.

Melting point: 88° C.

$^1$H-NMR(DMSO-d6/TMS): δ=1.55-2.24(8H,m) 2.88(2H, t,J=7 Hz) 7.81(8H,m) 11.10-12.90(1H,br)

(3) N-hydroxy-4,5-bis[4-(trifluoromethyl)phenyl]-2-oxazolehexanamide (Compound 7)

The desired subject compound was produced in the same manner as in the section (3) of example 1.

Melting point: 151° C.

$^1$H-NMR(DMSO-d6/TMS): δ=1.51-1.99(8H,m) 2.88(2H, t,J=7 Hz) 7.81(8H,m) 8.99-10.95(2H,br)

EXAMPLE 8

Production of 5-(4-fluorophenyl)-N-hydroxy-4-phenyl-2-thiazolehexanamide (Compound 8)

(1) 5-(4-fluorophenyl)-4-phenyl-2-thiazolehexanoic acid ethyl ester ethyl 6-(chloroformyl)hexanoate (3.18 g) and triethylamine (4.5 mL) were added to 2-amino-1-(4-fluorophenyl)-2-phenylethanone hydrochloride (3.98 g) in 1,3-dimethyl-2-imidazolidinone (90 mL), and the resultant mixture was reacted at room temperature for 2.5 hours. Ethyl acetate (400 mL) was added to the reaction liquid, the resultant mixture washed with diluted hydrochloric acid, water, saturated sodium hydrogen carbonate and a saturated saline solution sequentially in this order, and the organic solvent layer was dried by magnesium sulfate, and then filtered. The filtrate was condensed under a reduced pressure, the residue was added to a silica gel column (chloroform) to obtain an amide compound (5.93 g, Y=99%).

Diphosphoric pentasulfide (2.0 g) was added to the amide compound (2.86 g) in toluene (90 mL), and the resultant mixture was reacted at 80° C. for 2 hours. Toluene (100 mL) and water (100 mL) were added to the reaction liquid, the resultant mixture was subjected to liquid separation, and the organic layer washed with water, and then dried by magnesium sulfate. The resultant product was filtered, then condensed under a reduced pressure, and added to a silica gel column (chloroform) to obtain the subject compound (1.325 g, Y=46.6%).

$^1$H-NMR(CDCl$_3$/TMS): δ=1.25(3H,t,J=7 Hz) 1.40-2.01 (6H,m) 2.34(2H,t,J=6 Hz) 3.05(2H,t,J=7 Hz) 4.13(2H,q,J=7 Hz) 6.84-7.58(9H,m)

(2) 5-(4-fluorophenyl)-4-phenyl-2-thiazolehexanoic acid

25% aqueous sodium hydroxide (6 mL) was added to the compound (1.31 g) obtained in the above section (1) in methanol (60 mL), and the resultant mixture was reacted at room temperature over night. The reaction liquid was condensed under a reduced pressure, the residue was dissolved in water (100 mL), the resultant solution was then subjected to acidic precipitation with diluted hydrochloric acid, and a precipitated crystal was taken by filtration and dried to obtain the subject compound (1.116 mg, Y=91.6%).

Melting point: 135° C.

$^1$H-NMR(DMSO-d6/TMS): δ=1.30-1.91(6H,m) 2.24(2H, t,J=6 Hz) 3.01(2H,t,J=7 Hz) 7.20-7.50(9H,m) 11.98(1H,brs)

(3) 5-(4-fluorophenyl)-N-hydroxy-4-phenyl-2-thiazolehexanamide (Compound 8)

The compound (821 mg) obtained in the above section (2) was reacted with thionyl chloride (0.25 mL) in toluene (50 mL) under reflux for 1.5 hours to obtain an acid chloride.

A solution obtained by dissolving the obtained acid chloride in toluene (15 mL) was added to a methanol (15 mL) solution of hydroxylamine hydrochloride (1.0 g) and triethylamine (1.8 mL), and the resultant mixture was reacted at room temperature for 3.5 hours. The reaction liquid was condensed under a reduced pressure, and the residue was added to a silica gel column (chloroform) to obtain the desired subject compound (766 mg, Y=90%).

Melting point: 114° C.

$^1$H-NMR(DMSO-d6/TMS): δ=1.29-2.11(8H,m) 3.00(2H, t,J=7 Hz) 7.05-7.50(9H,m) 8.66(1H,brs) 10.24(1H,brs)

EXAMPLE 9

Production of 5-(4-chlorophenyl)-N-hydroxy-4-phenyl-2-thiazolehexanamide (Compound 9)

(1) 5-(4-chlorophenyl)-4-phenyl-2-thiazolehexanoic acid ethyl ester

The subject compound was produced in the same manner as in the section (1) of example 8.

$^1$H-NMR(CDCl$_3$/TMS): δ=1.25(3H,t,J=7 Hz) 1.40-2.04 (6H,m) 2.34(2H,t,J=6 Hz) 3.05(2H,t,J=7 Hz) 4.13(2H,q,J=7 Hz) 7.26-7.59(9H,m)

(2) 5-(4-chlorophenyl)-4-phenyl-2-thiazolehexanoic acid

The subject compound was produced in the same manner as in the section (2) of example 8.

Melting point: 157° C.

$^1$H-NMR(DMSO-d6/TMS): δ=1.30-1.90(6H,m) 2.24(2H, t,J=6 Hz) 3.01(2H,t,J=7 Hz) 7.37(9H,m) 11.99(1H,brs)

(3) 5-(4-chlorophenyl)-N-hydroxy-4-phenyl-2-thiazolehexanamide (Compound 9)

The desired subject compound was produced in the same manner as in the section (3) of example 8.

Melting point: 140° C.

$^1$H-NMR(DMSO-d6/TMS): δ=1.28-2.12(8H,m) 3.01(2H, t,J=7 Hz) 7.37(9H,m) 8.71(1H,brs) 10.24(1H,brs)

EXAMPLE 10

Production of N-hydroxy-5-(4-methylphenyl)-4-phenyl-2-thiazolehexanamide (Compound 10)

(1) 5-(4-methylphenyl)-4-phenyl-2-thiazolehexanoic acid ethyl ester

The subject compound was produced in the same manner as in the section (1) of example 8.

$^1$H-NMR(CDCl$_3$/TMS): δ=1.24(3H,t,J=7 Hz) 1.40-1.98 (6H,m) 2.23-2.45(5H,m) 3.03(2H,t,J=7 Hz) 4.13(2H,q,J=7 Hz) 7.01-7.60(9H,m)

(2) 5-(4-methylphenyl)-4-phenyl-2-thiazolehexanoic acid

The subject compound was produced in the same manner as in the section (2) of example 8.

Melting point: 143° C.

$^1$H-NMR(DMSO-d6/TMS): δ=1.25-1.91(6H,m) 2.13-2.35(5H,m) 2.99(2H,t,J=7 Hz) 7.19-7.49(9H,m) 11.96(1H, brs)

(3) N-hydroxy-5-(4-methylphenyl)-4-phenyl-2-thiazolehexanamide (Compound 10)

The subject compound was produced in the same manner as in the section (3) of example 8.

Melting point: 117° C.

$^1$H-NMR(DMSO-d6/TMS): δ=1.23-2.10(8H,m) 2.31(3H, s) 3.00(2H,t,J=7 Hz) 7.19-7.50(9H,m) 8.85(1H,brs) 10.27 (1H,brs)

EXAMPLE 11

Production of 4-(4-fluorophenyl)-N-hydroxy-5-phenyl-2-thiazolehexanamide (Compound 11)

(1) 4-(4-fluorophenyl)-5-phenyl-2-thiazolehexanoic acid ethyl ester

Diphosphoric pentasulfide (1.2 g) was added to ethyl 7-amino-7-oxoheptanoate (3.5 g) in toluene (180 mL), the resultant mixture was stirred at 50° C. for 1 hour, a toluene (30 mL) solution of 2-bromo-1-(4-fluorophenyl)-2-phenylethanone (3.48 g) was then added to the mixture, and the resultant mixture was reacted at the same temperature over night. Ethyl acetate (200 mL) and aqueous sodium hydroxide were added to the reaction liquid, and the resultant mixture was stirred, and then subjected to liquid separation. The organic layer washed with water, dried by magnesium sulfate, and then filtered. The filtrate was condensed under a reduced pressure, and the residue was added to a silica gel column (chloroform) to obtain the subject compound (1.814 mg).

(2) 4-(4-fluorophenyl)-5-phenyl-2-thiazolehexanoic acid

A 20% aqueous sodium hydroxide (5 mL) solution was added to the compound (1.81 g) obtained in the above section (1) in methanol (50 mL), and the resultant mixture was reacted at room temperature for 1.5 hours. The reaction liquid was condensed under a reduced pressure, the residue was dissolved in water (50 mL), the resultant solution was then subjected to acidic precipitation with diluted hydrochloric acid, and a precipitated crystal was taken by filtration and dried to obtain the subject compound (779 mg).
Melting point: 92° C.
$^1$H-NMR(DMSO-d6/TMS): δ=1.25-1.92(6H,m) 2.24(2H, t,J=6 Hz) 3.01(2H,t,J=7 Hz) 6.98-7.60(9H,m)

(3) 4-(4-fluorophenyl)-N-hydroxy-5-phenyl-2-thiazolehexanamide (Compound 11)

The compound (645 mg) obtained in the above section (2) was reacted with thionyl chloride (0.2 mL) in toluene (40 mL) under reflux for 1.5 hours. The reaction liquid was condensed under a reduced pressure to obtain an acid chloride.
A solution obtained by dissolving the obtained acid chloride in toluene (12 mL) was added to a methanol (12 mL) solution of hydroxylamine hydrochloride (0.8 g) and triethylamine (1.6 mL), and the resultant mixture was reacted at room temperature for 2 hours. The reaction liquid was condensed under a reduced pressure, ethyl acetate (80 mL) was added to the residue, and washed with water, and the organic layer was then dried by magnesium sulfate, and filtered. The filtrate was condensed under a reduced pressure, and the residue was then added to a silica gel column (chloroform/methanol) to obtain the desired subject compound (533 mg, Y=79.4%).
Melting point: 145° C.
$^1$H-NMR(DMSO-d6/TMS): δ=1.24-2.13(8H,m) 3.01(2H, t,J=7 Hz) 6.98-7.60(9H,m) 8.80(1H,brs) 10.32(1H,brs)

EXAMPLE 12

Production of 4-(4-chlorophenyl)-N-hydroxy-5-phenyl-2-thiazolehexanamide (Compound 12)

(1) 4-(4-chlorophenyl)-5-phenyl-2-thiazolehexanoic acid ethyl ester

The subject compound was produced in the same manner as in the section (1) of example 11.

(2) 4-(4-chlorophenyl)-5-phenyl-2-thiazolehexanoic acid

The subject compound was produced in the same manner as in the section (2) of example 11.
Melting point: 114° C.
$^1$H-NMR(DMSO-d6/TMS): δ=1.30-1.91(6H,m) 2.24(2H, t,J=6 Hz) 3.02(2H,t,J=7 Hz) 7.38-7.40(9H,m) 11.94(1H,brs)

(3) 4-(4-chlorophenyl)-N-hydroxy-5-phenyl-2-thiazolehexanamide (Compound 12)

The desired subject compound was produced in the same manner as in the section (3) of example 11.
Melting point: 126° C.
$^1$H-NMR (DMSO-d6/TMS): δ=1.23-2.12(8H,m) 3.00 (2H,t,J=7 Hz) 7.38-7.40(9H,m) 8.70(1H,brs) 10.31(1H,brs)

EXAMPLE 13

Production of N-hydroxy-4-(4-methylphenyl)-5-phenyl-2-thiazolehexanamide (Compound 13)

(1) 4-(4-methylphenyl)-5-phenyl-2-thiazolehexanoic acid ethyl ester

The subject compound was produced in the same manner as in the section (1) of example 11.

(2) 4-(4-methylphenyl)-5-phenyl-2-thiazolehexanoic acid

The subject compound was produced in the same manner as in the section (2) of example 11.
Melting point: 92° C.
$^1$H-NMR(DMSO-d6/TMS): δ=1.38-1.91(6H,m) 2.12-2.30(5H,m) 3.00(2H,t,J=7 Hz) 7.02-7.41(9H,m)

(3) N-hydroxy-4-(4-methylphenyl)-5-phenyl-2-thiazolehexanamide (Compound 13)

The desired subject compound was produced in the same manner as in the section (3) of example 11.
Melting point: 111° C.
$^1$H-NMR(DMSO-d6/TMS): δ=1.30-2.10(8H,m) 2.28(3H, s) 3.00(2H,t,J=7 Hz) 7.03-7.41(9H,m) 8.63(1H,brs) 10.30 (1h,brs)

EXAMPLE 14

Production of N-hydroxy-4,5-diphenyl-2-thiazolehexanamide (Compound 14)

(1) 4,5-diphenyl-2-thiazolehexanoic acid ethyl ester

The subject compound was produced in the same manner as in the section (1) of example 11.

(2) 4,5-diphenyl-2-thiazolehexanoic acid

The subject compound was produced in the same manner as in the section (2) of example 11.
Melting point: 126° C.
$^1$H-NMR(DMSO-d6/TMS): δ=1.30-1.92(6H,m) 2.24(2H, t,J=7 Hz) 3.01(2H,t,J=7 Hz) 7.35(10H,m)

(3) Production of N-hydroxy-4,5-diphenyl-2-thiazolehexanamide (Compound 14)

The desired subject compound was produced in the same manner as in the section (3) of example 11.
Melting point: 122° C.
$^1$H-NMR(DMSO-d6/TMS): δ=1.31-2.10(8H,m) 3.01(2H, t,J=7 Hz) 7.35(10H,m) 8.71(1H,brs) 10.28(1H,brs)

EXAMPLE 15

Production of N-hydroxy-5-phenyl-2-oxazolehexanamide (Compound 15)

(1) 5-phenyl-2-oxazolehexanoic acid ethyl ester

Triethylamine (3.5 g) and ethyl 6-(chloroformyl)hexanoate were added to aminoacetophenone hydrochloride (2.5 g) in 1,3-dimethyl-2-imidazolidinone (50 mL), and the resultant mixture was reacted at room temperature for 3 hours. Ethyl acetate (300 mL) was added to the reaction liquid, the resultant mixture was washed with water, and after the organic layer was then dried by magnesium sulfate. After filtration, the filtrate was condensed under a reduced pressure, and the residue was added to a silica gel column (toluene/ethyl acetate) to obtain an amide compound (3.037 g, Y=68.2%).

Diphosphoric pentasulfide (7.9 g) was added to the amide compound (3.037 g) in toluene (100 mL), and the resultant mixture was refluxed for 1.5 hours. Water (50 mL) was added to the reaction liquid, 20% aqueous sodium hydroxide was dropped into the resultant mixture under stirring to be neutralized, and the mixture was then subjected to liquid separation. The organic layer washed with water, and then dried by magnesium sulfate. An insoluble matter was filtered out, the filtrate was condensed under a reduced pressure, and the residue was then added to a silica gel column (toluene/ethyl acetate) to obtain the subject compound (1.174 g, Y=41.1%).
$^1$H-NMR(CDCl$_3$/TMS): δ=1.24(3H,t,J=7 Hz) 1.40-2.00 (6H,m) 2.32(2H,t,J=7 Hz) 2.84(2H,t,J=7 Hz) 4.13(2H,q,J=7 Hz) 7.10-7.70(5H,m)

(2) 5-phenyl-2-oxazolehexanoic acid

8% aqueous sodium hydroxide (10 mL) was added to the compound (1.11 g) obtained in the above section (1) in methanol (100 mL), and the resultant mixture was reacted at room temperature over night. The reaction liquid was condensed under a reduced pressure, the residue was dissolved in water (100 mL), and the resultant solution was then subjected to acidic precipitation with diluted hydrochloric acid. A precipitated crystal was taken by filtration, and dried to obtain the subject compound (904 mg, Y=90.2%).
Melting point: 100° C.
$^1$H-NMR(DMSO-d6/TMS): δ=1.25-1.98(6H,m) 2.22(2H, t,J=6 Hz) 2.80(2H,t,J=7 Hz) 7.30-7.80(6H,m) 11.97(1H,brs)

(3) N-hydroxy-5-phenyl-2-oxazolehexanamide (Compound 15)

Thionyl chloride (0.3 mL) was added to the compound (700 mg) obtained in the above section (2) in toluene (100 mL), and the resultant mixture was reacted under reflux for 1.5 hours. The reaction liquid was condensed under a reduced pressure to obtain an acid chloride.
A solution obtained by dissolving the obtained acid chloride in toluene (10 mL) was added to a methanol (20 mL) solution of hydroxylamine hydrochloride (1.2 g) and triethylamine (2.4 mL), and the resultant mixture was reacted at room temperature for 3 hours. The reaction liquid was condensed under a reduced pressure, and the residue was recrystallized from toluene to obtain the desired subject compound (510 mg, Y=68.9%).
Melting point: 129° C.
$^1$H-NMR(DMSO-d6/TMS): δ=1.35-2.10(8H,m) 2.80(2H, t,J=7 Hz) 7.30-7.78(6H,m) 8.63(1H,s) 10.31(1H,s)

EXAMPLE 16

Production of 5-(4-bromophenyl)-N-hydroxy-2-oxazolehexanamide (Compound 16)

(1) 5-(4-bromophenyl)-2-oxazolehexanoic acid ethyl ester

The subject compound was produced in the same manner as in the section (1) of example 15.

(2) 5-(4-bromophenyl)-2-oxazolehexanoic acid

The subject compound was produced in the same manner as in the section (2) of example 15.
Melting point: 124° C.

$^1$H-NMR(DMSO-d6/TMS): δ=1.49-2.35(8H,m) 2.80(2H, t,J=7 Hz) 7.60(1H,s) 7.65(4H,s) 11.47-12.57(1H,br)

(3) 5-(4-bromophenyl)-N-hydroxy-2-oxazolehexanamide (Compound 16)

The desired subject compound was produced in the same manner as in the section (3) of example 15.
Melting point: 131° C.
$^1$H-NMR(DMSO-d6/TMS): δ=1.47-1.97(8H,m) 2.80(2H, t,J=7 Hz) 7.60(1H,s) 7.65(4H,s) 8.64(1H,brs) 10.33(1H,brs)

EXAMPLE 17

Production of N-hydroxy-4-(4-methoxyphenyl)-2-oxazolehexanamide (Compound 17)

(1) 4-(4-methoxyphenyl)-2-oxazolehexanoic acid ethyl ester

Potassium carbonate (9.1 g) and 4-methoxyphenacyl bromide (5.0 g) were added to monoethyl pimerate (4.6 g) in DMF (50 mL), and the resultant mixture was reacted at room temperature for 5 hours. The reaction liquid was added to water (500 mL), the resultant mixture was stirred, and an object material was extracted with ethyl acetate (200 mL). The organic layer washed with water, dehydrated by magnesium sulfate, and then condensed under a reduced pressure to obtain an ester form (7.4 g).
Ammonium acetate (8.5 g) was added to the ester form (7.4 g) in acetic acid (50 mL), and the resultant mixture was reacted under reflux for 3 hours. The reaction liquid was condensed under a reduced pressure, water (100 mL) was added to the residue, and an object material was extracted with ethyl acetate (100 mL). The organic layer washed with water, dehydrated by magnesium sulfate, and then condensed under a reduced pressure to obtain a crude product. The crude product was purified with a silica gel column (chloroform) to obtain the subject compound (6.2 g, Y=89%).

(2) 4-(4-methoxyphenyl)-2-oxazolehexanoic acid

35% aqueous potassium hydroxide (10 mL) was added to the compound (6.2 g) obtained in the above section (1) in ethanol (40 mL), and the resultant mixture was reacted at room temperature for 3 hours. The reaction liquid was condensed under a reduced pressure, the residue was dissolved in water (70 mL) by heating, and the resultant solution was subjected to acidic precipitation by adding diluted hydrochloric acid. A precipitated crystal was taken by filtration, and washed with water to obtain a crude product. The crude product was recrystallized from ethanol to obtain the subject compound (2.67 g, Y=47%).
Melting point: 109° C.
$^1$H-NMR(DMSO-d6/TMS): δ=1.48-2.33(8H,m) 2.77(2H, t,J=7 Hz) 3.78(3H,s) 6.98(2H,d,J=9 Hz) 7.69(2H,d,J=9 Hz) 8.33(1H,s)

(3) N-hydroxy-4-(4-methoxyphenyl)-2-oxazolehexanamide (Compound 17)

The compound (500 mg) obtained in the above section (2) was reacted with thionyl chloride (0.3 mL) in dichloroethane (10 mL) under reflux. The reaction liquid was condensed under a reduced pressure, and then dissolved in 1,3-dimethyl- 2-imidazolidinone (15 mL) to obtain a 1,3-dimethyl-2-imidazolidinone solution of acid chloride.

The obtained 1,3-dimethyl-2-imidazolidinone solution of acid chloride was dropped into a 1,3-dimethyl-2-imidazolidinone (15 mL) solution of hydroxylamine hydrochloride (609 mg) and triethylamine (1.75 g), and the resultant mixture was reacted at room temperature for 3 hours. The reaction liquid was added to water (200 mL), diluted hydrochloric acid was added to pH=3, and an object material was then extracted with ethyl acetate (200 mL). The organic layer washed with water, dehydrated by magnesium sulfate, and then condensed under a reduced pressure to obtain a crude product. The crude product was purified by a silica gel column (chloroform/methanol) to obtain the subject compound (111 mg, Y=21%).

Melting point: 137° C.
$^1$H-NMR(DMSO-d6/TMS): δ=1.43-1.96(8H,m) 2.77(2H, t,J=7 Hz) 3.78 (3H,s) 6.98(2H,d,J=9 Hz) 7.69(2H,d,J=9 Hz) 8.33(1H,s) 8.42-9.16(1H,br) 9.88-10.73(1H,br)

EXAMPLE 18

Production of
4-(4-chlorophenyl)-N-hydroxy-2-oxazolehexanamide
(Compound 18)

(1) 4-(4-chlorophenyl)-2-oxazolehexanoic acid ethyl ester

The subject compound was produced in the same manner as in the section (1) of example 17.

(2) 4-(4-chlorophenyl)-2-oxazolehexanoic acid

The subject compound was produced in the same manner as in the section (2) of example 17.
Melting point: 83° C.
$^1$H-NMR(DMSO-d6/TMS): δ=1.49-2.32(8H,m) 2.79(2H, t,J=7 Hz) 7.63(4H,dd,J=9 Hz,20 Hz) 8.52(1H,s) 11.97(1H, brs)

(3) 4-(4-chlorophenyl)-N-hydroxy-2-oxazolehexanamide (Compound 18)

The desired subject compound was produced in the same manner as in the section (3) of example 17.
Melting point: 137° C.
$^1$H-NMR(DMSO-d6/TMS): δ=1.46-1.96(8H,m) 2.79(2H, t,J=7 Hz) 7.63(4H,dd,J=9 Hz,20 Hz) 8.53(1H,s) 8.68-10.46 (2H,br)

EXAMPLE 19

Production of
4-(4-fluorophenyl)-N-hydroxy-2-oxazolehexanamide
(Compound 19)

(1) 4-(4-fluorophenyl)-2-oxazolehexanoic acid ethyl ester

The subject compound was produced in the same manner as in the section (1) of example 17.

(2) 4-(4-fluorophenyl)-2-oxazolehexanoic acid

The subject compound was produced in the same manner as in the section (2) of example 17.
Melting point: 88° C.
$^1$H-NMR(DMSO-d6/TMS): δ=1.49-2.22(8H,m) 2.79(2H, t,J=7 Hz) 7.09-7.93(4H,m) 8.44(1H,s)

(3) 4-(4-fluorophenyl)-N-hydroxy-2-oxazolehexanamide (Compound 19)

The desired subject compound was produced in the same manner as in the section (3) of example 17.
Melting point: 133° C.
$^1$H-NMR(DMSO-d6/TMS): δ=1.43-1.96(8H,m) 2.78(2H, t,J=7 Hz) 7.10-7.93(4H,m) 8.45(1H,s) 8.59-10.60(2H,br)

EXAMPLE 20

Production of
5-(4-bromophenyl)-N-hydroxy-2-thiazolehexanamide
(Compound 20)

(1) 5-(4-bromophenyl)-2-thiazolehexanoic acid ethyl ester

The subject compound was produced in the same manner as in the section (1) of example 8.
Melting point: 83° C.
$^1$H-NMR(CDCl$_3$/TMS): δ=1.26-2.05(9H,m) 2.60-3.13 (4H,m) 4.51(2H,q,J=7 Hz) 7.27-7.62(4H,m) 7.80(1H,s)

(2) 5-(4-bromophenyl)-2-thiazolehexanoic acid

The subject compound was produced in the same manner as in the section (2) of example 8.
Melting point: 96° C.
$^1$H-NMR(DMSO-d6/TMS): δ=1.27-1.86(6H,m) 2.22(2H, t,J=6 Hz) 2.98(2H,t,J=7 Hz) 7.61(4H,m) 8.09(1H,s) 11.96 (1H,s)

(3) 5-(4-bromophenyl)-N-hydroxy-2-thiazolehexanamide (Compound 20)

The desired subject compound was produced in the same manner as in the section (3) of example 8.
Melting point: 142° C.
$^1$H-NMR(DMSO-d6/TMS): δ=1.27-2.14(8H,m) 2.98(2H, t,J=7 Hz) 7.61(4H,s) 8.09(1H,s) 8.62(1H,s) 10.31(1H,s)

EXAMPLE 21

Production of
N-hydroxy-4,5-dipropyl-2-oxazolehexanamide
(Compound 21)

(1) 4,5-dipropyl-2-oxazolehexanoic acid ethyl ester

The subject compound was produced in the same manner as in the section (1) of example 1.
$^1$H-NMR(CDCl$_3$/TMS): δ=0.75-1.95(19H,m) 2.10-2.80 (8H,m) 4.13 (2H, q, J=7 Hz)

(2) 4,5-dipropyl-2-oxazolehexanoic acid

The subject compound was produced in the same manner as in the section (2) of example 1.
$^1$H-NMR(CDCl$_3$/TMS) δ=0.90(6H,t,J=7 Hz) 1.25-1.95 (10H,m) 2.20-2.85(8H,m) 6.81(1Hbrs)

(3) N-hydroxy-4,5-dipropyl-2-oxazolehexanamide (Compound 21)

The desired subject compound was produced in the same manner as in the section (3) of example 1.

¹H-NMR(DMSO-d6/TMS): δ=0.85(6H,t,J=7 Hz) 1.25-1.95(10H,m) 2.18-2.73(8H,m) 8.69(1H,brs) 10.29(1H,brs)

EXAMPLE 22

Production of N-hydroxy-5-methyl-4-phenyl-2-oxazolehexanamide (Compound 22)

(1) 5-methyl-4-phenyl-2-oxazolehexanoic acid ethyl ester

The subject compound was produced in the same manner as in the section (1) of example 17.
¹H-NMR(CDCl₃/TMS): δ=1.12-2.88(16H,m) 4.13(2H,q,J=7 Hz) 7.30-7.73(5H,m)

(2) 5-methyl-4-phenyl-2-oxazolehexanoic acid

The subject compound was produced in the same manner as in the section (2) of example 17.
Melting point: 98° C.
¹H-NMR(DMSO-d6/TMS): δ=1.48-2.84(13H,m) 7.32-7.75(5H,m) 11.39-12.65(1H,br)

(3) N-hydroxy-5-methyl-4-phenyl-2-oxazolehexanamide (Compound 22)

The desired subject compound was produced in the same manner as in the section (3) of example 17.
Melting point: 140° C.
¹H-NMR(DMSO-d6/TMS): δ=1.43-2.82(13H,m) 7.28-7.75(5H,m) 8.44-9.43(1H,br) 9.87-10.89(1H,br)

EXAMPLE 23

Production of N-hydroxy-4-methyl-5-phenyl-2-oxazolehexanamide (Compound 23)

(1) 4-methyl-5-phenyl-2-oxazolehexanoic acid ethyl ester

The subject compound was produced in the same manner as in the section (1) of example 15.
¹H-NMR(CDCl₃/TMS): δ=1.24(3H,t,J=7 Hz) 1.40-1.96(6H,m) 2.20-2.53(5H,m) 2.79(2H,t,J=7 Hz) 4.12(2H,q,J=7 Hz) 7.20-7.68(5H,m)

(2) 4-methyl-5-phenyl-2-oxazolehexanoic acid

The subject compound was produced in the same manner as in the section (2) of example 15.
Melting point: 113° C.
¹H-NMR(DMSO-d6/TMS): δ=1.25-1.85(6H,m) 2.11-2.32(5H,m) 2.75(2H,t,J=7 Hz) 7.30-7.65(5H,m) 11.95(1H,brs)

(3) N-hydroxy-4-methyl-5-phenyl-2-oxazolehexanamide (Compound 23)

The desired subject compound was produced in the same manner as in the section (3) of example 15.
Melting point: 112° C.
¹H-NMR(DMSO-d6/TMS): δ=1.25-2.11(8H,m) 2.32(3H,s) 2.74(2H,t,J=7 Hz) 7.30-7.65(5H,m) 8.64(1H,s) 10.33(1H,s)

EXAMPLE 24

Production of N-hydroxy-4,5-diphenyl-2-oxazoleheptanamide (Compound 24)

Using 4,5-diphenyl-2-oxazoleheptanoic acid (653 mg), a reaction and a treatment were carried out in the same manner as in the section (3) of example 1 to obtain the desired subject compound 24 (530 mg, Y=77.8%).
Melting point: 109° C.
¹H-NMR(DMSO-d6/TMS): δ=1.20-2.10(10H,m) 2.83(2H,t,J=7 Hz) 7.46(10H,m) 8.66(1H,brs) 10.28(1H,brs)

EXAMPLE 25

Production of N-hydroxy-4,5-diphenyl-2-oxazolehexanamide (Compound 25)

(1) 4,5-diphenyl-2-oxazolehexanoic acid ethyl ester

The subject compound was produced in the same manner as in the section (1) of example 1.
¹H-NMR(CDCl₃/TMS): δ=1.24(3H,t,J=7 Hz) 1.36-2.00(6H,m) 2.34(2H,t,J=6 Hz) 2.87(2H,t,J=7 Hz) 4.13(2H,q,J=7 Hz) 7.20-7.75(10H,m)

(2) 4,5-diphenyl-2-oxazolehexanoic acid

The subject compound was produced in the same manner as in the section (2) of example 1.
Melting point: 112° C.
¹H-NMR(DMSO-d6/TMS): δ=1.25-1.90(6H,m) 2.24(2H,t,J=6 Hz) 2.84(2H,t,J=7 Hz) 7.46(10H,m)

(3) N-hydroxy-4,5-diphenyl-2-oxazolehexanamide (Compound 25)

The desired subject compound was produced in the same manner as in the section (3) of example 1.
Melting point: 142° C.
¹H-NMR(DMSO-d6/TMS): δ=1.27-2.00(8H,m) 2.83(2H,t,J=7 Hz) 7.46(10H,m) 8.66(1H,brs) 10.33(1H,brs)

The compounds obtained in the examples described above are shown in Table 1. Compound numbers correspond to those given to compounds in the examples.

TABLE 1

Structure: A-thiazole(with Y)-B, with -(CH₂)ₙ-CONHOH substituent

| Compound number | Y | A | B | n |
|---|---|---|---|---|
| 1 | O | phenyl | 4-(tert-butyl)phenyl | 5 |
| 2 | O | phenyl | 4-Cl-phenyl | 5 |
| 3 | O | phenyl | 4-F-phenyl | 5 |
| 4 | O | 4-Me-phenyl | 4-Me-phenyl | 5 |
| 5 | O | 4-MeO-phenyl | 4-MeO-phenyl | 5 |
| 6 | O | 4-F-phenyl | 4-F-phenyl | 5 |
| 7 | O | 4-F₃C-phenyl | 4-F₃C-phenyl | 5 |
| 8 | S | phenyl | 4-F-phenyl | 5 |
| 9 | S | phenyl | 4-Cl-phenyl | 5 |
| 10 | S | phenyl | 4-Me-phenyl | 5 |
| 11 | S | 4-F-phenyl | phenyl | 5 |
| 12 | S | 4-Cl-phenyl | phenyl | 5 |
| 13 | S | 4-Me-phenyl | phenyl | 5 |
| 14 | S | phenyl | phenyl | 5 |
| 15 | O | H | phenyl | 5 |
| 16 | O | H | 4-Br-phenyl | 5 |
| 17 | O | 4-MeO-phenyl | H | 5 |
| 18 | O | 4-Cl-phenyl | H | 5 |
| 19 | O | 4-F-phenyl | H | 5 |
| 20 | S | H | 4-Br-phenyl | 5 |
| 21 | O | n-propyl | n-propyl | 5 |
| 22 | O | phenyl | Me | 5 |
| 23 | O | Me | phenyl | 5 |

TABLE 1-continued

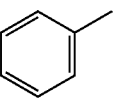

| Compound number | Y | A | B | n |
|---|---|---|---|---|
| 24 | O | 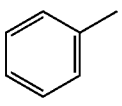 | 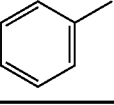 | 6 |
| 25 | O | 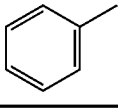 | | 5 |

PREPARATION EXAMPLE 1

| Production of tablet | |
|---|---|
| Compound of the present invention | 10.0 g |
| Lactose | 9.0 g |
| Hydroxypropylcellulose | 2.0 g |
| Crystalline cellulose | 7.7 g |
| Magnesium stearate | 0.3 g |
| Talc | 1.0 g |

A tablet containing 100 mg of compound of the present invention can be produced by a conventional method using the above composition.

TEST EXAMPLE 1

Measurement of IL-6 and TNFα production suppressing activities

Tests were conducted with reference to the method by G. Lozanski et al. (J. Rheumatol., Vol. 19, 921-926, 1992).

Using a 10% fetal calf serum (FCS)-added PRMI-1640 medium, THP-1 cells (Dainippon Pharmaceutical Co., Ltd.) were prepared in an amount of $10^6$/mL, and inoculated on a 48-well microplate in an amount of 500 μL per well. $10^{-8}$ M of phorbol 12-myristate 13-acetate (PMA) was added to the wells, and the cells were cultured for 24 hours to induce differentiation of the cells to macrophages.

50 μL of test substance diluting liquid or DMSO diluting liquid was added to the wells, and the cells were preincubated by a $CO_2$ incubator at 37° C. for 30 minutes. 5 μL of LPS (111 μg/mL) (final concentration: 1 μg/mL) was added to each well. Furthermore, wells with no LPS added to the DMSO diluting liquid were set. After the cells were cultured for 24 hours, they were centrifuged to take cell supernatants, and the IL-6 level was measured using the Human IL-6 ELISA kit (Biosource International), and TNFα was measured using the Human tumor necrosis factor-α ELISA kit (Biosource International), by the enzyme-linked immunosorbent assay (ELISA). The results are shown in Tables 2 and 3.

TABLE 2

Results of IL-6 production suppression test

| Test substance | Active concentration (M) | IL-6 production suppression rate (%) |
|---|---|---|
| Example 20 | $1 \times 10^{-6}$ | 64 |
| Example 24 | $1 \times 10^{-7}$ | 50 |
| Example 25 | $1 \times 10^{-7}$ | 50 |

TABLE 3

Results of TNFα production suppression test

| Test substance | Active concentration (M) | TNFα production suppression rate (%) |
|---|---|---|
| Example 8 | $1 \times 10^{-6}$ | 40 |
| Example 20 | $1 \times 10^{-7}$ | 44 |

As apparent from the results shown in Tables 2 and 3, the compounds of the present invention exhibited strong production suppressing activities against IL-6 and/or TNFα.

For reference, the IL-6 and TNFα production suppressing activities of the compound (4,5-diphenyl-2-oxazolehexanoic acid) obtained in the section (2) of example 25, which is a carboxylic acid derivative of example 25, were evaluated. The compound showed no activity in a range of concentrations ($1 \times 10^{-5}$--$^9$ M) with which the tests were conducted.

TEST EXAMPLE

Evaluation of Cytotoxicity

Cytotoxicity was evaluated by the MTT method.

Specifically, a 0.5 mg/mL solution of 3-(4,5-dimethyl-2-thiazolyl)-2,5-diphenyl-2H-tetrazolium bromide (MTT, Sigma) prepared in a 10% fetal calf serum (FCS)-added PRMI-1640 medium was added in an amount of 100 μL per well to cells with culture supernatants removed in test example 1, and the cells were cultured for 3 hours. The culture solution was removed by centrifugal separation, 100 μL of methanol was added to each well, and the absorbance was measured at a wavelength of 570 nm after cytolysis.

The absorbances for the well to which the DMSO diluting liquid was added and the well to which no LPS was added are 100% and 0%, respectively, the absorbances for wells of different doses of test substances are expressed as percentages, and the results are shown in Table 4.

TABLE 4

Results of cytotoxicity test

| Test substance | Concentration (M) | | | | |
|---|---|---|---|---|---|
| | $1 \times 10^{-9}$ | $1 \times 10^{-9}$ | $1 \times 10^{-7}$ | $1 \times 10^{-6}$ | $1 \times 10^{-5}$ |
| Example 8 | 106.7 | 105.3 | 106.7 | 113.7 | 88.9 |
| Example 20 | 95.6 | 104.0 | 102.0 | 97.6 | 82.3 |
| Example 24 | 96.4 | 83.9 | 88.1 | 91.8 | 83.8 |
| Example 25 | 85.8 | 91.9 | 87.6 | 83.6 | 78.9 |

As apparent from the results shown in Table 4, none of the test compounds tested in test example 1 showed strong cytotoxicity in concentrations used.

INDUSTRIAL APPLICABILITY

The compounds of the present invention suppress production of IL-6 and (or) TNFα of inflammatory cytokines, while they have low toxicity to cells. Therefore, the compounds of the present invention are useful as prophylactics or therapeutics for various kinds of inflammatory diseases, septicemia, multiple myeloma, osteoporosis, chronic rheumatoid arthritis, Castleman disease, inflammatory colitis, autoimmune disease and the like.

What is claimed is:
1. A Compound represented by formula (1):

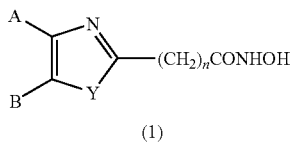

[Formula 1]

(1)

wherein A and B, which are the same or different, each represent an aryl group which may have a substituent, Y represents an oxygen atom or a sulfur atom, and n represents an integer of 5 or 6,
or pharmaceutically acceptable salts thereof.

2. The compound according to claim 1, wherein in formula 1, A and B, which are the same or different, each are a phenyl group, or a phenyl group substituted with a halogen atom, a lower alkyl group, a lower alkoxy group or a halogenated lower alkyl group, or pharmaceutically acceptable salts thereof.

3. The compound according to claim 1 selected from the group of compounds listed below:
5-[4-(1,1-dimethylethyl)phenyl]-N-hydroxy-4-phenyl-2-oxazolchexanamide,
5-(4-chlorophenyl)-N-hydroxy-4-phenyl-2-oxazolehexanamide,
5-(4-fluorophenyl)-N-hydroxy-4-phenyl-2-oxazolehexanamide,
N-hydroxy-4,5-bis(4-methylphenyl)-2-oxazolchexanamide,
N-hydroxy-4,5-bis(4-methoxyphenyl)-2-oxazolehexanamide,
4,5-bis(4-fluorophenyl)-N-hydroxy-2-oxazolehexanamide,
N-hydroxy-4,5-bis[4-(trifluoromethyl)phenyl]-2-oxazolchexanamide,
5-(4-fluorophenyl)-N-hydroxy-4-phenyl-2-thiazolchexanamide,
5-(4-chlorophenyl)-N-hydroxy-4-phenyl-2-thiazolehexanamide,
N-hydroxy-5-(4-methylphenyl)-4-phenyl-2-thiazolehexanamide,
4-(4-fluorophenyl)-N-hydroxy-5-phenyl-2-thiazolehexanamide,
4-(4-chlorophenyl)-N-hydroxy-5-phenyl-2-thiazolehexanamide,
N-hydroxy-4-(4-methylphenyl)-5-phenyl-2-thiazolehexanamide,
N-hydroxy-4,5-diphenyl-2-thiazolehexanamide,
N-hydroxy-4,5-diphenyl-2-oxazoleheptanamide, and
N-hydroxy-4,5-diphenyl-2-oxazolehexanamide,
or pharmaceutically acceptable salts thereof.

4. A medicine having as an active ingredient the compound according to claim 1, or pharmaceutically acceptable salts thereof.

5. An inhibitor of the production of interleukin 6 and/or TNFα having as an active ingredient the compound according to claim 1, or pharmaceutically acceptable salts thereof.

6. A medicine having as an active ingredient the compound according to claim 2, or pharmaceutically acceptable salts thereof.

7. A medicine having as an active ingredient the compound according to claim 3, or pharmaceutically acceptable salts thereof.

8. An inhibitor of the production of interleukin 6 and/or TNFα having as an active ingredient the compound according to claim 2, or pharmaceutically acceptable salts thereof.

9. An inhibitor of the production of interleukin 6 and/or TNFα having as an active ingredient the compound according to claim 3, or pharmaceutically acceptable salts thereof.

10. A method for inhibiting the production of interleukin 6 and/or TNFα in an animal body including a human body, which comprises administering to the animal body a compound represented by formula (1):

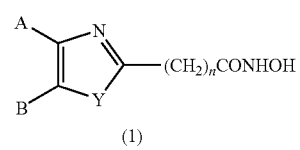

[Formula 1]

(1)

wherein A and B, which are the same or different, each represent an aryl group which may have a substituent, Y represents an oxygen atom or a sulfur atom, and n represents an integer of 5 or 6, or pharmaceutically acceptable salts thereof.

11. The method according to claim 10, wherein in formula 1, A and B, which are the same or different, each are a phenyl group, or a phenyl group substituted with a halogen atom, a lower alkyl group, a lower alkoxy group or a halogenated lower alkyl group, or pharmaceutically acceptable salts thereof.

12. The method according to claim 10, wherein n is an integer of 5 or 6, or pharmaceutically acceptable salts thereof.

13. The method according to claim 10, wherein the compound represented by formula (1) is selected from the group of compounds listed below:
5-[4-(1,1-dimethylethyl)phenyl]-N-hydroxy-4-phenyl-2-oxazolchexanamide,
5-(4-chlorophenyl)-N-hydroxy-4-phenyl-2-oxazolehexanamide,
5-(4-fluorophenyl)-N-hydroxy-4-phenyl-2-oxazolehexanamide,
N-hydroxy-4,5-bis(4-methylphenyl)-2-oxazolehexanamide,
N-hydroxy-4,5-bis(4-methoxyphenyl)-2-oxazolehexanamide,
4,5-bis(4-fluorophenyl)-N-hydroxy-2-oxazolchexanamide,
N-hydroxy-4,5-bis[4-(trifluoromethyl)phenyl]-2-oxazolchexanamide,
5-(4-fluorophenyl)-N-hydroxy-4-phenyl-2-thiazolehexanamide, 5-(4-chlorophenyl)-N-hydroxy-4-phenyl-2-thiazolehexanamide,
N-hydroxy-5-(4-methylphenyl)-4-phenyl-2-thiazolehexanamide,
4-(4-fluorophenyl)-N-hydroxy-5-phenyl-2-thiazolehexanamide,
4-(4-chlorophenyl)-N-hydroxy-5-phenyl-2-thiazolehexanamide,
N-hydroxy-4-(4-methylphenyl)-5-phenyl-2-thiazolehexanamide,
N-hydroxy-4,5-diphenyl-2-thiazolehexanamide,
N-hydroxy-4,5-diphenyl-2-oxazoleheptanamide, and
N-hydroxy-4,5-diphenyl-2-oxazolehexanamide,
or pharmaceutically acceptable salts thereof.

* * * * *